United States Patent
Thurston et al.

(10) Patent No.: US 6,442,996 B1
(45) Date of Patent: Sep. 3, 2002

(54) METHOD AND APPARATUS FOR MEASURING THE CALORIFIC VALUE OF A GAS

(75) Inventors: Robert Richard Thurston, Melbourne; Paul Stephen Hammond, Ashby de la Zouch; Barry Leonard Price, Quorn, all of (GB)

(73) Assignee: Lattice Intellectual Property Limited, London (GB)

( * ) Notice: Subject to any disclaimer, the term of this patent is extended or adjusted under 35 U.S.C. 154(b) by 0 days.

(21) Appl. No.: 09/581,558

(22) PCT Filed: Jan. 8, 1999

(86) PCT No.: PCT/GB99/00069

§ 371 (c)(1),
(2), (4) Date: Aug. 29, 2000

(87) PCT Pub. No.: WO99/36767

PCT Pub. Date: Jul. 22, 1999

(30) Foreign Application Priority Data

Jan. 16, 1998 (GB) ............................................. 9800822
Jul. 15, 1998 (GB) ............................................. 9815255

(51) Int. Cl.$^7$ ................................................. G01N 29/02
(52) U.S. Cl. ................... 73/24.01; 73/24.06; 73/25.03; 73/25.05; 73/30.04; 73/31.05; 73/23.31; 374/31; 374/36
(58) Field of Search ............................ 73/24.01, 24.05, 73/30.01, 24.06, 30.04, 25.01, 25.03, 25.05, 23.31, 31.05; 374/31, 36, 37

(56) References Cited

U.S. PATENT DOCUMENTS

| 4,246,773 A | 1/1981 | Haruta .................... 73/24.01 |
| 4,938,066 A | 7/1990 | Dorr |
| 5,537,854 A | 7/1996 | Phillips et al. ............. 73/24.01 |
| 6,047,589 A | 4/2000 | Hammond et al. ........ 73/24.01 |

FOREIGN PATENT DOCUMENTS

| EP | 0 715 169 | 6/1996 | ................ 73/24.01 |
| GB | 2 312 508 | 10/1997 | ................ 73/24.01 |

*Primary Examiner*—Daniel S. Larkin
(74) *Attorney, Agent, or Firm*—Oblon, Spivak, McClelland, Maier & Neustadt, P.C.

(57) ABSTRACT

A method and apparatus for measuring the calorific value of a gas. The apparatus includes a chamber to which a gas in question, for example natural gas, is supplied through an inlet and leaves through an outlet. The speed of sound SoS at ambient temperature is measured using any suitable method such as electronic control and a calculating device and an ultra-sound emitter and an ultra-sound receiver. The ambient temperatures $T_a$, is observed by a temperature sensor, and a thermal conductivity sensor measures the thermal conductivity of the gas at two different temperatures above the ambient temperature. One value $ThC_H$, of the thermal conductivity is measured at 70° C. above ambient and the other value $ThC_L$ of the thermal conductivity is measured at 50° C. above ambient. The control calculates the calorific value CV of the gas according to the formula:

$$CV = a \cdot ThC_H + b \cdot ThC_L + C \cdot SoS + d \cdot T_a + e \cdot T_a^2 + f,$$

where a, b, c, d, e and f are constants.

25 Claims, 1 Drawing Sheet

METHOD AND APPARATUS FOR MEASURING THE CALORIFIC VALUE OF A GAS

FIELD OF THE INVENTION

This invention relates to a method and apparatus for measuring the calorific value of a gas.

The gas may be a fuel gas, for example natural gas. The natural gas may be methane and may further comprise nitrogen and/or carbon dioxide. In addition to methane the natural gas may comprise at least one other hydrocarbon gas, for example ethane, propane, butane, pentane or hexane.

SUMMARY OF THE INVENTION

According to one aspect of the invention, a method of measuring the calorific value of a gas comprises making a measure of the speed of sound in the gas and using the speed of sound in an operation producing the calorific value corresponding to said speed of sound.

According to another aspect of the invention a method of measuring the calorific value of a gas comprises making a measure of the speed of sound in the gas, making a measure of a first thermal conductivity of the gas at a first temperature, making a measure of a second thermal conductivity of the gas at a second temperature which differs from the first temperature, and using the speed of sound and the first and second thermal conductivities in an operation producing the calorific value of the gas corresponding to said speed of sound and said first and second thermal conductivities.

According to a further aspect of the invention an apparatus to measure the calorific value of a gas comprises means to measure the speed of sound in the gas and means to use the speed of sound in an operation producing the calorific value of the gas corresponding to said speed of sound.

According to a still further aspect of the invention an apparatus to measure the calorific value of a gas comprises means to measure a first thermal conductivity of the gas at a first temperature; means to measure a second thermal conductivity of the gas at a second temperature which differs from the first temperature, and means using the speed of sound and the first and second thermal conductivities in an operation producing the calorific value of the gas corresponding to said speed of sound and said first and second thermal conductivities.

BRIEF DESCRIPTION OF THE DRAWINGS

The invention will now be further described, by way of example, with reference to the accompanying drawings in which.

DESCRIPTION OF THE PREFERRED EMBODIMENTS

Figure 1:
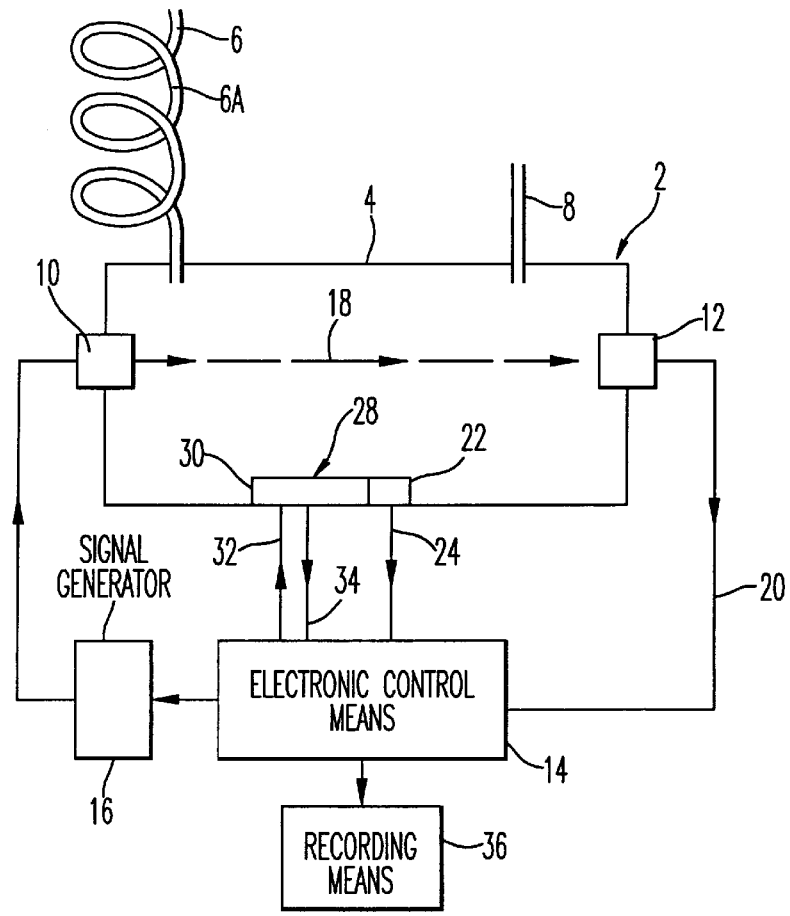
FIG. 1 diagrammatically shows an apparatus in which the invention can be performed.

With reference to FIG. 1, an apparatus 2 to measure the calorific value of a gas has a chamber 4 into which the gas is supplied through an inlet conduit 6 and leaves through an outlet conduit 8. The inlet conduit 6 includes heat exchange means 6A, for example, a copper coil, by which the temperature of the incoming gas can be adjusted to a value substantially the same as that of the ambient temperature of the external atmosphere, whereby the gas in the chamber 4 is of substantially uniform temperature throughout. The chamber 4 includes an ultrasound emitter transducer 10 and an ultrasound receiver transducer 12. An electronic control means 14 including computer means is connected to a signal generator 16 so that under the control of the control means 14 the signal generator causes the transducer 10 to emit ultrasound signals 18 as desired. The ultrasound signals 18 are received by the transducer 12 and their reception signaled to the control means 14 via line 20. The time of flight of the ultrasonic signals between transducers 10 and 12 is measured by the control means 14 which is arranged to calculate SOS which is the speed of sound in metres/second (m/s).

If desired some other means of measuring the speed of sound in the gas may be used, such as that disclosed in U.S. Pat. No. 4,938,066. However, the most preferable method is that disclosed in UK patent application Nos. GB 9813509.8, GB 9813513.0 and GB 9813514.8. These applications disclose the use of a resonator to measure the speed of sound of a gas within the resonator. A driving electronic circuit which may include or be in the form of a microprocessor is arranged to produce a sinusoidal signal over a suitable range of frequencies to drive a loudspeaker. The loudspeaker is arranged to apply an acoustic signal to the interior of a resonator. A microphone is arranged to detect the magnitude of the acoustic signal within the resonator. The signal from the microphone is filtered and amplified by an appropriate electronic circuit and a processing means determines the resonant frequency relating to the gas within the resonator to determine its speed of sound.

A temperature sensor 22 in the chamber 4 provides the control-means 14 with data on line 24 representing the value of the ambient temperature.

The ambient temperature sensor 22 may be part of a thermal conductivity sensor 28 comprising thermal conductivity observation means 30. The thermal conductivity sensor 28 may be a miniature thermal conductivity microsensor model type TCS208 available from Hartmann & Braun AG of Frankfurt am Main, Germany.

The thermal conductivity observation means 30 used to observe the thermal conductivity of the gas has heater means which in response to signals on line 32 from the control means 14 can operate at more than one selected desired temperature above the ambient temperature observed by the sensor 22, and a signal representative of the thermal conductivity of the gas at the desired temperature is sent to the control means on line 34.

The control means 14 is arranged to cause the thermal conductivity sensor 28 to measure the thermal conductivity of the gas at two different desired temperatures $t_H$ and $t_L$ in which $t_H$, is a pre-determined desired number of temperature degrees $t_1$, above the ambient temperature observed by the sensor 22 and $t_L$ is a predetermined desired number of temperature degrees $t_2$, above ambient temperature; the number $t_1$, being greater than the number $t_2$.

Using the observed or measured values of the speed of sound in the gas, the thermal conductivity of the gas at temperature $t_H$ and $t_L$ and the observed value of the ambient temperature of the gas by sensor 22, the control means 14 calculates the calorific value of the gas using the formula $$CV = a \cdot ThC_H + b \cdot ThC_L + C \cdot SoS + d \cdot T_a + e \cdot T_a^2 + f \qquad -I$$

in which

CV is the calorific value;

ThC$_H$ is the thermal conductivity of the gas at temperature t$_H$;

ThC$_L$ is the thermal conductivity of the gas at temperature t$_L$;

SoS is the speed of sound in the gas at the ambient temperature;

T$_a$ is the ambient temperature of the gas observed by the sensor 22, and a, b, c, d, e and f are respective constants.

The gas in question may be a mixture of two or more gases in which the composition of the mixture may be of variable proportions. For example the gas in question may be a fuel gas. Such a fuel gas may be natural gas. The natural gas may comprise methane and at least one of ethane, propane, butane, pentane or hexane, and may further comprise nitrogen and/or carbon dioxide.

In order to derive the constants a, b, c, d, e, and f in equation I, the mathematical technique known as regression analysis may be used in respect of data collected in connection with the gas in question. The proportions of gases in the mixture may be varied to form a number of different samples. Using chromatographic methods, the calorific value CV of a sample is obtained, the ambient temperature T$_3$, of the sample is measured, and the thermal activities ThC$_H$ and ThC$_L$ of the sample are measured. This is done for each sample in turn to obtain a set of measured values corresponding to each sample. The sets of values are inserted in equation I and the "best-fit" values for constants a, b, c, d, e and f are derived. In the case of natural gas coming ashore at a number of locations in the United Kingdom, regression analysis was performed on samples from the different locations and also on gas equivalence groups which are artificial replications in the laboratory of mixtures of methane and ethane, methane and butane, methane and pentane, and methane and hexane in which, in the laboratory, those mixtures are represented by different mixtures of methane and propane.

When equation I was applied to natural gas and to gas equivalence groups and regression analysis used, the following values for the constants were derived, namely:

a=36.25649, b=−45.5768, c=0.047029 d=0.091067, e=0.00074, and f=24.18731, when

CV is the calorific value of gas in MJ/m$^3_{st}$(Megajoules/ standard cubic metres);

ThC$_H$ is the thermal conductivity of the gas in W/m.K (where K is degrees Kelvin) at a temperature of substantially 70 degrees Celsius above ambient temperature T$_a$;

ThC$_L$ is the thermal conductivity of the gas in W/m.K at a temperature t$_L$ which is substantially 50 degrees Celsius above ambient temperature T$_a$;

SoS is the speed of sound in the gas in m/s, and T$_a$ is the ambient temperature of the gas in degrees Celsius.

In the above application of equation I to natural gas, the value of t$_1$, is substantially 70° C. and the value of t$_1$ is substantially 50° C. Thus the difference between the temperatures t$_H$ and t$_L$ at which the thermal conductivities ThC$_H$ and ThC$_L$ are measured differ by substantially 20° C. [(T$_a$+70)−(T$_a$+50)=20].

The value of the calorific value CV of the gas calculated by the control means 14 may be visually displayed and/or printed or otherwise recorded by recording means 36 in response to signals from the control means.

By any suitable technique know per se the control means 16 may be provided with information representing the relative density of the gas or the control means may be provided with information enabling it to calculate the relative density RD of the gas. The control means 14 may calculate or otherwise obtain the value of the Wobble Index WI of the gas using the formula.

$$WI = \frac{CV}{\sqrt{RD}}$$

A method of measuring relative density is described in our co-pending British patent application No. GB9715448.8 filed on Jul. 22, 1997.

When fuel gas is combusted in a process (e.g. furnace, kiln, compressor, engine, etc.) some form of control system is used to set the oxygen (in this case in the form of air)/fuel gas ratio to ensure optimum combustion. An allowance is made in the amount of excess air to account in part, for variations in fuel gas composition changes. This allowance means that the process is running less efficiently than it could do because extra air is being heated and vented.

However, a measure of the calorific value or Wobbe Index, which is indicative of the fuel gas quality and which may be found according to the present invention, may be used in a feed forward control strategy to improve the accuracy of control available and achieve better efficiency.

Figure 2:
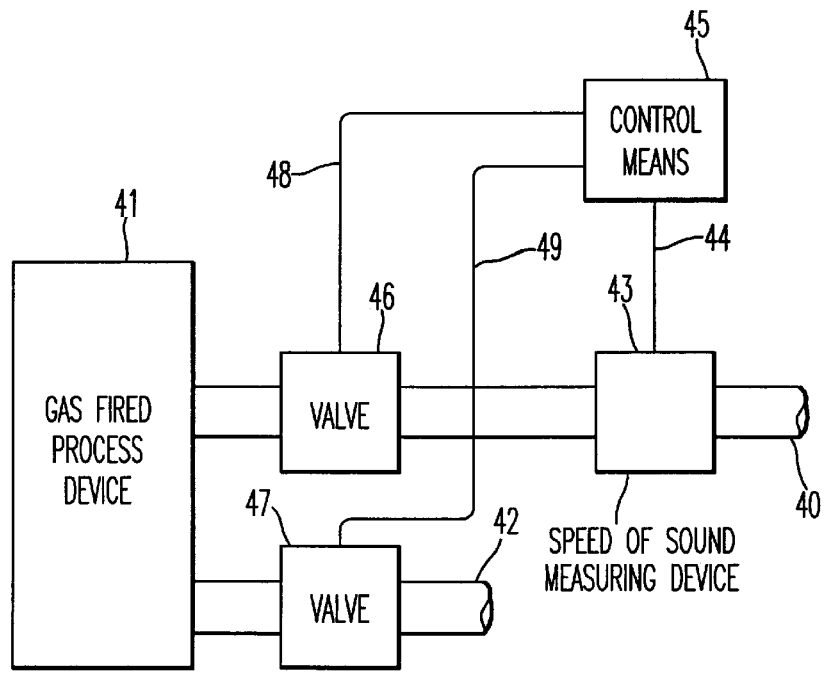
FIG. 2 shows a diagrammatic example of a feed forward air/fuel gas control system utilising the present invention.

An apparatus to perform such control is shown in FIG. 2. Fuel gas is supplied via a conduit 40, such as a pipe, to a gas fired process 41, such as a furnace, kiln, a compressor or an engine and oxygen in the form of air is supplied to the process 41 via another conduit 42. Any suitable device 43 which may be in the form of one or more probes temporarily insert able into the conduit 40 or as one or more permanent fixtures is arranged to measure the speed of sound of the fuel gas passing through the conduit 40, the thermal conductivities of the gas ThC$_H$, ThC$_L$ at two temperatures t$_H$ and t$_L$, and the ambient temperature of the gas T$_a$, The speed of sound of the fuel gas SOS, the thermal conductivities ThC$_H$, and ThC$_L$, and the ambient temperature of the gas T$_a$ are measured by device 43 and passed via a connection 44 to a control means 45, which may be a microprocessor or a computer for example. Control means 45 determines the calorific value of the fuel gas from the received measurements from device 43 as explained earlier. Having determined a measure of the gas quality, the control means is able to adjust the air/fuel gas ratio setpoint using an oxygen/fuel gas ratio control system 46, 47 to achieve better efficiency. In this case the oxygen/fuel gas control system comprises two variable opening valves 46, 47 one in each of the fuel gas and air conduits 40, 42 respectively and both controlled by the control means 45 via connections 48, 49. Alternatively, the oxygen/fuel gas control system could comprise a variable opening valve on just one of conduits 40, 42.

What is claimed is:

1. A method of measuring the calorific value of a gas comprising:

making a measure of a first thermal conductivity of the gas at a first temperature, making a measure of a second thermal conductivity of the gas at a second temperature which differs from the first temperature, and using a speed of sound and the first and second thermal conductivities in an operation producing the calorific value of the gas corresponding to said speed of sound and said first and second thermal conductivities.

2. A method as claimed in claim 1, in which the calorific value is obtained by a procedure involving use of the formula:

$$CV = a \cdot ThC_H + b \cdot ThC_L + C \cdot SoS + d \cdot T_a + e \cdot T_a^2 + f,$$

where CV is the calorific value of the gas, where $ThC_H$ is the first thermal conductivity of the gas at said first temperature, where $ThC_L$ is the second thermal conductivity of the gas at said second temperature which is lower than said first temperature, where SoS is the speed of sound in gas at ambient temperature, and where $T_a$ is the ambient temperature of said gas whereof said thermal conductivities are measured, the first and second temperatures being greater than said ambient temperature, and a, b, c, d, e, and f are constants.

3. A method as claimed in claim 2, in which SoS is the speed of sound in m/s, the thermal conductivities are in units of Watts/metre x degrees Kelvin (W/m.k), the temperature $T_a$ and the first and second temperatures are in degrees Celsius, and the calorific value is in megajoules/standard cubic metre ($MJ/m^3_{st}$).

4. A method as claimed in claim 2, in which the gas is fuel gas.

5. A method as claimed in claim 4, in which the fuel gas is natural gas.

6. A method as claimed in claim 3, in which the gas is natural gas comprising at least one hydrocarbon gas which is methane, and said natural gas further comprises nitrogen and/or carbon dioxide.

7. A method as claimed in claim 7, in which:

a is substantially 36.25649, b is substantially −45.5768, c is substantially 0.047029, d is substantially 0.091067, e is substantially 0.00074, and f is substantially 24.18731.

8. A method as claimed in claim 2, in which the first temperature is substantially 70° C. above ambient temperature.

9. A method as claimed in claim 2, in which the second temperature is substantially 50° C. above the ambient temperature.

10. A method of measuring the Wobbe index of gas using the formula $$WI = \frac{CV}{\sqrt{RD}}$$

in which WI is the Wobbe index, RD is the relative density of the gas, and CV is the calorific value obtained by the method as claimed in claim 1.

11. An apparatus to measure the calorific value of a gas comprising:

means to measure a first thermal conductivity of the gas at a first temperature;

means to measure a second thermal conductivity of the gas at a second temperature which differs from the first temperature; and means using a speed of sound and the first and second thermal conductivities in an operation producing the calorific value of the gas corresponding to said speed of sound and said first and second thermal conductivities.

12. An apparatus as claimed in claim 11, in which the calorific value is obtained by a procedure involving use of the formula:

$$CV = a \cdot ThC_H + b \cdot ThC_L + C \cdot SoS + d \cdot T_a + e \cdot T_a^2 + f,$$

where CV is the calorific value of the gas, where $ThC_H$ is the first thermal conductivity of the gas at said first temperature, where $ThC_L$ is the second thermal conductivity of the gas at said second temperature which is lower than said first temperature, where SoS is the speed of sound in gas at ambient. temperature, and where $T_a$ is the ambient temperature of said gas whereof said thermal conductivities are measured, the first and second temperatures being greater than said ambient temperature, and a, b, c, d, e and f are constants.

13. An apparatus as claimed in claim 12, in which SoS is the speed of sound in m/s, the thermal conductivities are in units of Watts/metre x degrees Kelvin (W/m.k), the temperature $T_3$ and the first and second temperatures are in degrees Celsius, and the calorific value is in megajoules/ standard cubic metre ($MJ/m^3_{st}$).

14. An apparatus as claimed in claim 13, in which the gas is natural gas comprising at least one hydrocarbon gas which is methane, and said natural gas further comprises nitrogen and/or carbon dioxide.

15. An apparatus as claimed in claim 14, in which:

a is substantially 36.25649, b is substantially −45.5768, c is substantially 0.047029, d is substantially 0.091067, e is substantially 0.00074, and f is substantially 24.18731.

16. An apparatus as claimed in claim 12, in which the gas is fuel gas.

17. An apparatus as claimed in claim 16, in which the fuel gas is natural gas.

18. An apparatus as claimed in claim 12, in which the first temperature is substantially 70° C. above ambient temperature.

19. An apparatus as claimed in claim 12, in which the second temperature is substantially 50° C. above the ambient temperature.

20. A control means for adjusting the oxygen/fuel gas ratio of a gas fired process comprising an apparatus for measuring the calorific value of a fuel gas for the gas fired process according to claim 11, and means for adjusting an oxygen/fuel gas ratio control system for the gas fired process in accordance with the measured calorific value.

21. A furnace comprising means for receiving a supply of oxygen; means for receiving a supply of fuel gas; an oxygen/fuel gas ratio control system; and a control means according to claim 20.

22. A kiln comprising means for receiving a supply of oxygen; means for receiving a supply of fuel gas; an oxygen/fuel gas ratio control system; and a control means according to claim 20.

23. A compressor comprising means for receiving a supply of oxygen; means for receiving a supply of fuel gas; an oxygen/fuel gas ratio control system; and a control means according to claim 20.

24. An engine comprising means for receiving a supply of oxygen; means for receiving a supply of fuel gas; an oxygen/fuel gas ratio control system; and a control means according to claim 20.

25. An apparatus to measure the Wobbe index of gas using the formula $$WI = \frac{CV}{\sqrt{RD}}$$

in which WI is the Wobbe index, RD is the relative density of the gas, and CV is the calorific value obtained using an apparatus as claimed in claim 11.

* * * * *